Jan. 19, 1960 E. S. BOERNER Plant Pat. 1,898
ROSE PLANT
Filed May 4, 1959
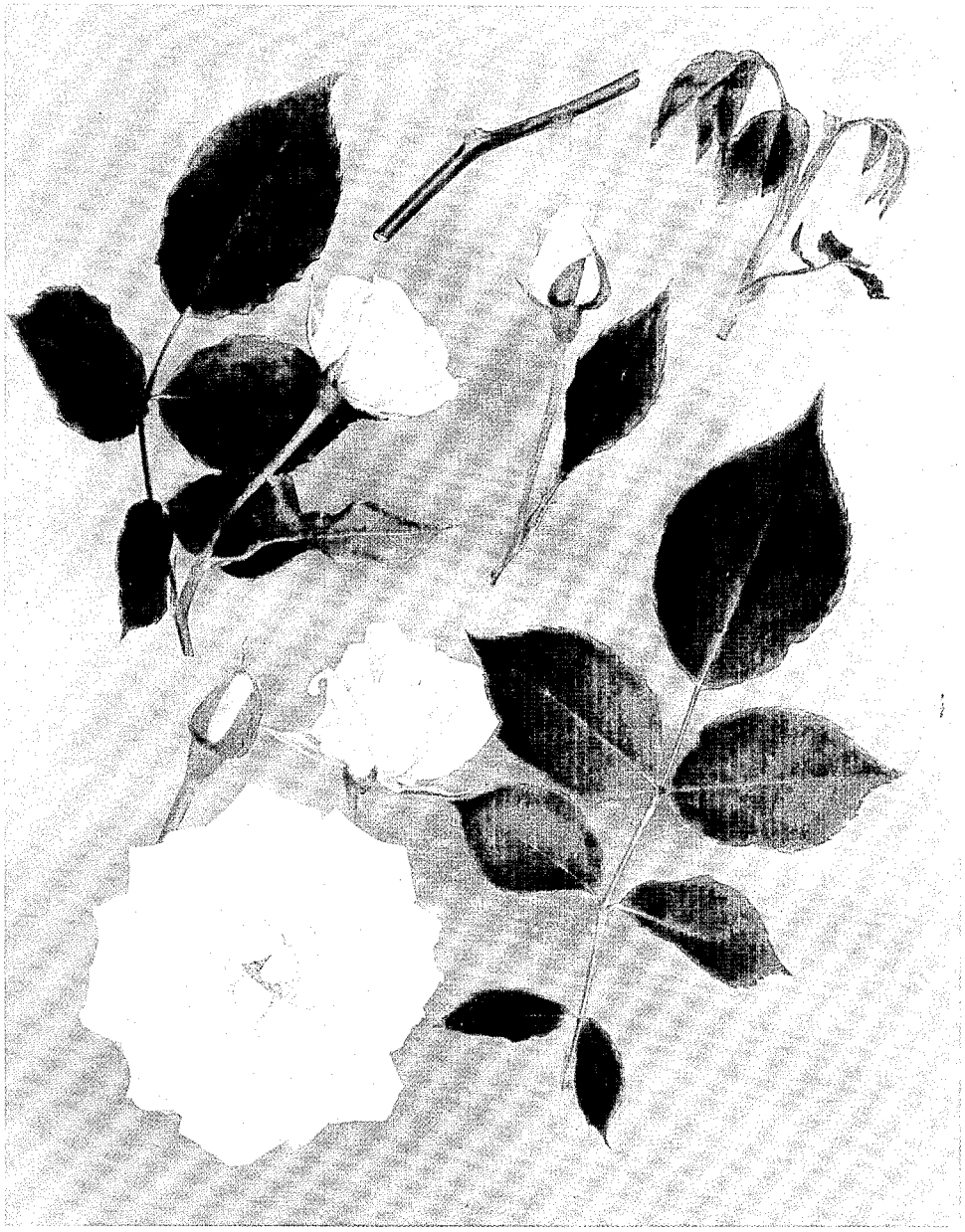
Inventor.
E. S. Boerner
By: Robb & Robb
Attorneys.

United States Patent Office

Plant Pat. 1,898

Patented Jan. 19, 1960

1,898

ROSE PLANT

Eugene S. Boerner, Newark, N.Y., assignor to Jackson & Perkins Company, Newark, N.Y., a corporation of New York Application May 4, 1959, Serial No. 810,977

1 Claim. (Cl. 47—61)

The present invention relates to a new and distinct variety of rose plant of the floribunda class, which was originated by me by crossing an unnamed and unpatented seedling derived from a cross of "Goldilocks" (Plant Patent No. 672) × a seedling of an unknown origin, with the variety "Tawny Gold" (Plant Patent No. 950).

The primary objective of this breeding was to produce a new and improved floribunda rose which bears flowers of a yellow color and having long-lasting qualities. This objective was fully achieved, along with other desirable improvements, through the use of the unnamed seedling aforementioned as the seed parent, this seedling being characterized by its excellent forcing value, its straight stems and stiff flower petals, but which required crossing with a rose of deeper yellow color to achieve a true yellow forcing floribunda. The variety "Tawny Gold" was utilized as the pollen parent to attain the desired color in the new variety, as well as a heavy fragrance. The new combination of features resulting from this breeding represents a unique floribunda rose which is distinguished from its parents, as well as from all other varieties of which I am aware, as evidenced by the following outstanding characteristics:

(1) An unusual and interesting habit of developing a large leaf immediately above the first leaflet under the bud;

(2) A distinctive Empire Yellow general color tonality of the flowers, with the edges of the flower petals lightly overcast with Light Cadmium;

(3) A distinctive and intense fruity fragrance of the flowers; and (4) Excellent lasting qualities of the flowers when cut.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Goldilocks" × a seedling of unknown origin.

*Pollen parent.*—"Tawny Gold."

Classification:

*Botanic.*—Floribunda.

*Commercial.*—Floribunda.

*Flower*

(Observations made from specimens grown in a greenhouse at Newark, New York, in the early morning during the early part of January.)

Blooming habit: Recurrent—continuous.

Bud:

*Size.*—medium.

*Form.*—Ovoid; is not affected by wet or hot weather.

*Color.*—When sepals first divide—Light Greenish Yellow, Plate 5. When petals being to unfurl—Light Cadmium, Plate 4. When half-blown: inside of petals—Apricot Yellow, Plate 4, with lower half of petals lightly overcast with Empire Yellow, Plate 4; reverse of petals—Apricot Yellow, Plate 4, with lower half of petals lightly overcast with Light Cadmium, Plate 4.

*Sepals.*—Slightly branched; curl back when petals begin to unfurl. Color: inside—Kildare Green, Plate 31; outside—Bice Green, Plate 17.

*Calyx.*—Color—Bice Green, Plate 17. Shape—Pear. Size—small. Aspect—smooth. Odor when rubbed: none.

*Peduncle.* — Length — medium. Aspect — smooth. Strength—erect; slender. Color—Absinthe Green, Plate 31.

*Opening.*—Opens up well; is not affected by adverse weather conditions.

Bloom:

*Size.*—Medium. Average size when fully expanded—3¼ inches.

*Borne.*—Several together, and in irregular clusters.

*Stems.*—Medium length; strong.

*Form (when first open).*—Cupped. Permanence—flattens.

*Petalage.*—Double (full but open center). Number of petals under normal conditions—from 30 to 35.

*Color.*—Center of flower—Pinard Yellow, Plate 4, lightly overcast with Light Cadmium, Plate 4. Outer petals—Pinard Yellow, Plate 4. Base of petals (aiglet)—Lemon Yellow, Plate 4. Inside of petals—Empire Yellow, Plate 4, with edge of petals lightly overcast with Light Cadmium, Plate 4. Reverse of petals—Baryta Yellow, Plate 4. General tonality from a distance—Empire Yellow, Plate 4, with edges of petals Light Cadmium, Plate 4.

*Discoloration.*—General tonality at end of first day—Empire Yellow, Plate 4, lightly overcast with Light Cadmium, Plate 4. Second day—Pinard Yellow, Plate 4, lightly overcast with Light Cadmium, Plate 4. Third day—Pinard Yellow, Plate 4, lightly overcast with Light Cadmium, Plate 4.

Petals:

*Texture.*—Thick; is not affected by wet or hot weather.

*Appearance.*—Inside—satiny. Outside—shiny.

*Form.*— Oval.

*Arrangement.*—Imbricated (regularly arranged shinglelike).

*Petaloids in center.*—Few; small.

*Persistence.*—Drop off cleanly.

*Fragrance.*—Strong. Nature—fruity (russet apple).

*Lasting quality.*—On the plant—very long. As cut flower—very long.

*Genital organs*

Stamens, anthers: Medium size; many; regularly arranged around styles. Color—Apricot Yellow, Plate 4.

Stamens, filaments (threads): Medium length. Color—Picric Yellow, Plate 4.

Pollen: Color—Martius Yellow, Plate 4.

Styles: Bunched; uneven length; medium length; thin.

Stigmas: Color—Light Orange Yellow, Plate 3.

Ovaries: All enclosed in calyx.

Hips: None.

Seeds: None.

*Plant*

Form: Bush.

Growth: Vigorous; upright; branching.

Foliage: Compound of 5 to 7 leaflets, and with a large leaf immediately above the first leaflet under the bud.

*Size.*—Large.

*Quantity.*—Abundant.

*Color.*—New foliage: upper side—Grass Green, Plate 6, with mid-rib of Parrot Green, Plate 6, and serrations of Oxblood Red, Plate 1; under side—Biscay Green, Plate 17, lightly overcast with Pompeian Red, Plate 13. Old foliage: upper side—Cedar Green, Plate 6; under side—Light Bice Green, Plate 17.

*Shape.*—Oval pointed.

*Texture.*—Upper side—leathery; glossy. Under side—smooth.

*Ribs and veins.*—Ordinary.

*Edge.*—Serrated (saw toothed).

*Serrations.*—Single; small.

*Leaf stem.*—Color—Absinthe Green, Plate 31. Under side—prickly.

*Stipules.*—Medium length; smooth.

Wood:

*New wood.*—Color—Lettuce Green, Plate 5. Bark—smooth.

*Old wood.*—Color—Cress Green, Plate 31. Bark—smooth.

Thorns:

*Thorns.*—Quantity: on main stalks from base—few; on laterals from stalk—few. Form—narrow base; short; hooked downward. Color (when young)—Chartreuse Yellow, Plate 31. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by an unusual habit of developing a large leaf immediately above the first leaflet under the bud, a distinctive Empire Yellow general color tonality of the flowers, with the edges of the flower petals lightly overcast with Light Cadmium, a distinctive and intense fruity fragrance of the flowers, and the long-lasting quality of the flowers when cut.

No references cited.